United States Patent [19]

Hagel et al.

[11] 4,250,294
[45] Feb. 10, 1981

[54] POLYMERS OBTAINED FROM POLYNITROAROMATIC COMPOUNDS

[75] Inventors: Rainer Hagel, Lichtenfels; Klaus Redecker, Nuremberg, both of Fed. Rep. of Germany

[73] Assignee: Dynamit Nobel Aktiengesellschaft, Troisdorf, Fed. Rep. of Germany

[21] Appl. No.: 962,865

[22] Filed: Nov. 22, 1978

[30] Foreign Application Priority Data

Nov. 23, 1977 [DE] Fed. Rep. of Germany ....... 2752166

[51] Int. Cl.$^3$ ............................................. C08G 83/00
[52] U.S. Cl. ................................. 528/210; 44/15 R; 44/25; 568/931; 548/152; 548/191; 260/315; 260/346.22; 549/49; 549/68; 564/155; 564/433; 568/932; 544/198; 568/935; 544/209; 544/237; 544/296; 546/102; 546/103; 546/109; 568/585; 568/586; 528/86; 528/368; 528/369; 528/377; 528/378; 528/403; 528/417; 528/422; 528/423

[58] Field of Search ................. 528/423, 422, 86, 210, 528/417, 403, 368, 369, 377, 378; 260/219.1, 302 H, 304 D, 315, 346.22, 558 R, 576, 645, 646; 544/198, 209, 237, 296; 546/102, 103, 109; 549/57, 59; 568/585, 586

[56] References Cited

U.S. PATENT DOCUMENTS

| | | | |
|---|---|---|---|
| 2,726,217 | 12/1955 | Hubbard | 528/422 |
| 3,808,276 | 4/1974 | Confort et al. | 528/422 |
| 3,974,121 | 8/1976 | Wong | 528/422 |

*Primary Examiner*—Lester L. Lee
*Attorney, Agent, or Firm*—Sprung, Felfe, Horn, Lynch & Kramer

[57] ABSTRACT

A polymer having aromatic or heterocyclic rings as the only structural elements said aromatic or heterocyclic rings containing at least two nitro groups is disclosed as well as a method of preparing the same. The polymers are useful as binding agents for thermo stable propellants and can be easily formed into films. They remain thermally stable up to temperatures of at least 200° C.

20 Claims, No Drawings

POLYMERS OBTAINED FROM POLYNITROAROMATIC COMPOUNDS

BACKGROUND OF THE INVENTION

1. Field of the Invention

This invention relates to polymers having aromatic and/or heterocyclic rings as structural elements. More especially, this invention relates to certain thermally stable polymers useful as binding agents for thermo stable propellents, said polymers being thermally stable up to temperatures of at least 200° C. This invention also relates to a method of preparing these polymers.

2. Discussion of the Prior Art

In U.S. Pat. No. 3,755,471, polynitro aromatics are described in which nitrated phenyl rings are joined together. These compounds are crystalline, highly explosive and sensitive to shock. They are, however, still thermally stable at 250° C. These polynitro aromatic compounds are prepared by the reaction of a mono-chlorotrinitrobenzene (picryl chloride) with a dihalogen trinitrobenzene, the less reactive picryl chloride being employed in excess.

Unfortunately, the compounds of U.S. Pat. No. 3,755,471 are not suitable as binding agents for thermal stable propellents. Unlike nitrocellulose and polyvinyl nitrate, they do not form coherent films and they cannot readily be mixed with plasticizers. Their crystallinity also renders them unsuitable for the preparation of a binding agent.

It therefore becomes desirable to provide thermally stable compositions containing nitro groups which can be formed into polymers which polymers in turn can be formed into coherent films in the presence of plasticizers. More especially, it has become desirable to provide such thermally stable compositions in the form of polymers which can readily be mixed with plasticizers and yet maintain the thermal stability up to temperatures of at least 200° C. Still moreover, it has become desirable to provide such a polymer by an efficient inexpensive process which does not require the use of more than a single organic reactant. These and other objects of this invention are provided by the herein disclosed polymer.

SUMMARY OF THE INVENTION

Broadly, this invention contemplates a polymer having an aromatic or heterocyclic ring as the only structural element, said aromatic or heterocyclic ring containing at least two nitro groups.

Within the scope of the present invention, there are numerous polymers. Particularly contemplated polymers include homo polymers having a recurring unit of the formula

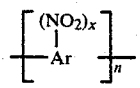

wherein x is 2 to 3, Ar is a more substituted or unsubstituted arylene radical or a substituted or unsubstituted divalent heterocyclic radical where the hetero atom is oxygen, nitrogen, sulphur.

Referring to the formula set forth above, contemplated arylene radicals include those formed from mononuclear aromatic compounds, e.g., phenylene as well as those divalent aryl radicals derived from fused ringed compounds such as naphthalene, phenanthrene and anthracene. Also contemplated are polynuclear arylene compounds where the rings are joined directly to one another by a carbon-to-carbon linkage or through an oxygen atom or through a moiety of the group

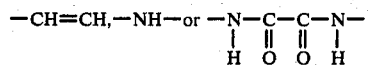

Generally speaking, the arylene radical will have between 6 and 14 carbocyclic carbon atoms. In addition to the nitro substitution depicted in the formula, the arylene group can be substituted by one or more of the following groups: $CH_3$, $OH$ or $OCH_3$.

Where Ar represents a divalent heterocyclic radical, the heterocyclic radical can contain between 3 and 13 carbocyclic carbon atoms, preferably between 3 and 8 carbocyclic carbon atoms. The heterocyclic radical can contain one or more hetero atoms including a mixture of different hetero atoms. Contemplated hetero atoms include oxygen, nitrogen, sulphur. Of these, it is preferred that the divalent hetercyclic radical have as at least one of the hetero atoms, an oxygen, nitrogen, or sulphur atom.

The polymers of the present invention are at least partially amorphous. Generally speaking, the polymers of the present invention contain between 4 and 20 recurring units, preferably between 4 and 12 recurring units. The molecular weight of the polymer depends upon the nature of the monomer employed to form the same. Generally speaking, the molecular weight is in the range of 800 to 4500, preferably between >800 and <2500, the molecular weight being determined by gel chromatography. (GPC).

The polymers of the present invention can be formed into films in the presence of plasticizers and they can form binding agents for thermo stable propellents. The polymers of the present invention are thermally stable to temperatures of at least 200° C., preferably to temperatures of at least 250° C.

Referring to the formula set forth above where Ar represents a divalent heterocyclic radical this heterocyclic radical can contain substituents as well. Substituents on the heterocyclic radical include: $CH_3$, $OH$, $OCH_3$.

Also contemplated within the definition of Ar are admixed aryl-heterocyclic radicals where the heterocyclic radical is fused to an arylene radical. Included within this definition are divalent radicals of compounds such as indene, benzofuran (Coumarone), thionaphthene (benzothiofuran), indole, indolenine. Where Ar is a divalent heterocyclic radical, a heterocyclic radical itself can be a fused heterocyclic radical such as 1,5-pyrindine, and the like.

Especially contemplated polymers of the invention are those having the recurring unit of the formula

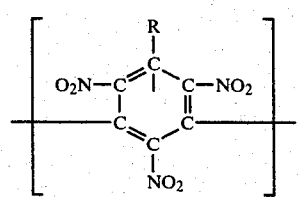

in which R can be hydrogen or methyl, OH or $OCH_3$.

Also contemplated in particular are polymers with a structural element of the formula

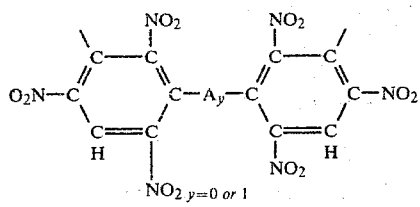

wherein A represents oxygen or a moiety of the group

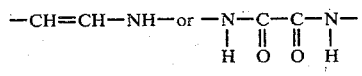

and y=0 or 1.

It will be noted, that the polymers of the present invention whether derived from aryl compound or heterocyclic compound have as the only structural element the aryl or heterocyclic ring. The aryl or heterocyclic ring contains at least 2 nitro groups.

The polymers of the invention do not have the abovedescribed disadvantages of polynitroterphenyl. They are noncrystalline compounds, they are stable up to about 250° C., and they can be made into films in the presence of plasticizers.

The new polymers are prepared in a known manner by the reaction di- or trihalopolynitro aryl or heterocyclic compound especially di or trichloro with copper at elevated temperatures. This reaction, known as the Ullmann reaction, has hitherto led to only dimeric or trimeric compounds (cf. F. Ullmann, J. Bielecki, Chem. Ber. 34 (1901) pp. 2174 to 2185). Polymeric compounds have never before been obtained by this reaction, even when 1,4-dichloro-2-nitro-benzene, for example, was used as the starting product.

It has additionally been found that only when the chlorine atoms are in the ortho position with respect to a nitro group can the condensation reaction which produces the new polymers result in polymeric compounds when dichloropolynitro aromatics are used. If dibromo- or diiodopolynitro aromatics are used, the position of the bromine or iodine atoms with respect to a nitro group is only of secondary importance.

The reaction is performed in the same range of temperatures as the Ullmann reaction. When chloropolynitro aromatics are the starting products, the reaction generally starts up only at temperatures above 150° C. and it can be conducted at temperatures up to 250° C. It is preferable, then, to operate at temperatures above 170° C. and up to 200° C. The dibromo and diiodo polynitro aromatics can react at lower temperatures, depending on the nature of the compounds. For these starting products, the lowermost temperature limit is considered to be 90° C. In general, however, the reaction of these starting products is also performed at temperatures above 150° C.

The copper is used preferably in the form of powder or chips. Copper alloys can also be used. The amount is between 1 and 10 gram-atoms of copper per halogen per mole of the halogen nitro compound. The preferred ratio is between 2:1 and 4:1.

The reaction is performed preferably in a solvent. Suitable solvents are inert, aromatic hydrocarbons of high boiling point, e.g., at least 200° C. which can also be nitrated, and whose melting point is to be below room temperature. Nitrobenzene is a preferred solvent.

The amount of solvent to be used should at least correspond to the weight of the polyhalogen polynitro compound. It can amount to as much as twenty times the weight of the starting product. The preferred ratio of solvent to the polyhalogen polynitro compound is between 3:1 and 12:1.

The usable polyhalogen polynitro compounds include halogen nitro compounds which are derived from mononuclear or polynuclear aromatic or heterocyclic compounds. Examples of the mononuclear aromatic compounds are the dihalogen compounds of di- and trinitrobenzene or of the di- or trinitrotoluenes, such as dichlorotrinitroresorcinol or 3,5-dichloro-2,4,6-trinitrotoluene.

Acylation products of dichloronitro compounds can also be used.

The dinuclear aromatic compounds which can be used as starting products for the new polymers include the dichloropolynitro compounds of naphthalene and diphenyl, the two rings of the diphenyl being able to be joined together also by hetero atoms, as for example by oxygen, nitrogen, or a group from the series:

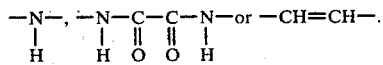

Examples are the following: 3,3'-dichloro-2,4,6,2',4',6'-hexanitro-diphenyl, dichlorohexanitrostilbene, dichlorohexanitrodiphenyloxide, dichlorohexanitrodiphenylamine.

Examples of polynuclear starting compounds are the dihalogen polynitro compounds of naphthalene, anthracene and phenanthrene.

The condensed polynuclear aromatic compounds can also contain hetero atoms, such as, for example, oxygen, nitrogen, or sulfur. Examples of such compounds are the chlorides of 1,3,6,8-tetranitrocarbazole or of 1,3,6,8-tetranitroacridone. Other aromatic compounds whose dichloropolynitro compounds can be used as starting products for the polymers of the invention are, for example, benzothiophene, benzothiazole, acridine, phenazine, and phthalazine.

Examples of heterocyclic compounds whose dichlorodinitro compounds can be used are thiophene, 1,3-thiazole, s-triazine, or pyrimidine, the last two compounds being used especially in condensed ring systems with benzene, chlorobenzenes, nitrobenzenes or chloronitrobenzenes.

The condensation of the di- and trichloropolynitro aromatic compounds to the new polymers is generally performed by absorbing or dissolving the halogen compound in the solvent. Thereafter, it is heated to the reaction temperature and the metal powder is added, preferably in portions. The reaction that sets in is exothermic, so that no further heating is necessary in some cases.

The end of the reaction is indicated by the fact that shiny metal particles are no longer visible, if the metal powder is used in amounts within the preferred range. If no more shiny metal particles are visible, the reaction mixture can continue to be held at the reaction temperature for a brief period, if desired; then it is cooled and a solvent for the polymer (e.g., acetone or ethyl acetate) is added for the purpose of separating it from copper halide, so formed the excess copper, and any insoluble by-products that may have formed. The filtrate is concentrated by evaporation and the polymer is extracted with a nonsolvent.

The raw polymer can be used directly as a binding agent for propellents which are stable at high temperatures. If, however, purer products are desired, the raw polymer is again washed or precipitated from a suitable solvents, e.g., nitrobenzene acetone, ether. In these operations the low-molecular-weight components of the polymer are dissolved out. If desired, any copper salt still present is washed out by treatment with hydrochloric acid and an aqueous ammonia solution.

The new polymers can have up to approximately 20 structural units. The low-molecular-weight condensates have at least four structural units.

In order to more fully illustrate the nature of the invention and in a manner of practicing the same, the following examples are presented.

EXAMPLES

Preparation of the Preliminary Products

Dipyridinium styphnate 500 grams (2.04 moles) of dry styphnic acid are added in portions, with vigorous stirring, to two liters of dry pyridine. The mixture warms up slightly and a yellow reaction product precipitates. The mixture is stirred for another hour in the warm state, and then the cooled mixture is freed of solids by filtration. The solids are washed with one liter of ether, suspended in two liters of ether, freed of the solvent by filtration, again washed with 500 ml of ether, and dried in air.

Yield: 730 g (88.7% of the theory) M.P. 165°-170° C. Styphnic acid dichloride 730 g (1.81 moles) of dipyridinium styphnate is added in portions, with stirring (initially without cooling), to 350 ml (3.82 moles) of $POCl_3$. The temperature rises, and is maintained at 70° C. by cooling. After all of the salt has been added, the mixture is heated for 30 minutes with continued stirring at 100° C., then cooled to 40° to 50° C., and then decomposed by adding it in portions to 3 liters of water with vigorous stirring. The temperature of the water is maintained at 30° C. by the addition of ice. After suction filtration, the residue is washed acid-free and dried in air.

Yield: 480 g (94.0% of the theory, melting range 122° to 126° C.

EXAMPLE 1

Polynitropolyphenylene 100 g (0.35 moles) of dry styphnic acid dichloride is added to 250 ml of anhydrous nitrobenzene and the mixture is heated at 170° C. 10 g of copper powder is added, and the mixture is heated with vigorous stirring at 180° C. When the exothermic reaction starts, the heating is removed and additional copper powder is added rapidly enough to enable the temperature to be maintained at 180° to 185° C. After a total of 70 g of copper powder has been added, some heating is required to bring the total amount of copper powder added to 140 g (2.2 g-atoms). Stirring is continued for an additional 30 minutes at 180° C., and then the mixture is cooled and 250 ml of acetone is added to dilute the mixture. The residue remaining (approximately 170 g), which consists mainly of copper chloride and metallic copper, is separated and washed with acetone (200 ml).

For further purification, the filtrates are combined and the solvents are removed in a rotary evaporator to the greatest possible extent, with the aid of an oil pump. The solid residue is extracted for 30 minutes with 500 ml of ether, with vigorous stirring and refluxing. Then it is filtered and the polymer is obtained as a black residue which still contains copper and which can be used as it is or can be treated for removal of the copper. For this purpose it is first treated with steam and then foamed with 300 ml of concentrated hydrochloric or nitric acid. The hydrochloric acid is allowed to act for one hour at room temperature, and then the mixture is suction filtered and the residue is stirred into 300 ml of a 1% aqueous ammonia solution. Filtration, washing and drying in vacuo yields 55 g of a polymer having a deflagration point of 278° C. Further testing resulted in the following elemental analysis:

| | |
|---|---|
| C | 36.49% |
| H | 1.18% |
| O | 44.29% |
| N | 18.04% |
| | 100.00% |

The sample, an 0.25% solution in THF, was tested in the Waters GPC 100 apparatus: peaks occurred at 16, 20, 28.5, 37 and 45 Å. (The information given herein on the molecule size in Ångstroms refers to the length of the outstretched chain and was obtained by comparison with aliphatic hydrocarbons.)

The chain length of a phenyl building block can be assumed to be about 3.6 Å; in the case of substituted phenyls, however, it may be slightly higher. The degree of oligomerization thus lies between about 4 and 11.

EXAMPLE 2

10 g (20 mmols) of 3,3'-dichloro-2,4,6,2',4',6'-hexanitrodiphenyl is heated in 30 ml of nitrobenzene at 180° C. At this temperature, 14 g (0.22 gram-atoms) of very fine copper powder is added, and then stirring is continued for ten minutes, the mixture is cooled, and 50 ml of acetone is added. The mixture is filtered and the filtrate is freed substantially of solvents by evaporation; 75 ml of ether is added, and it is refluxed for half an hour, then filtered, and the residue is dried at room temperature. 10 g of a polynitropolyphenylene is obtained having the properties described in Example 1. This product can be used either in a mold or, after treatment with plasticizers, it can be used, for example, as a heat-stable, energy-rich propellant binding agent.

What is claimed is:

1. A polymer having an aromatic or heterocyclic ring as the only structural element, said polymer containing at least 2 nitro groups on said aromatic or heterocyclic ring, the hetero atom of said hetercyclic ring being oxygen, nitrogen, or sulfur, the polymer having at least four recurring units and up to 20 recurring units said aromatic or heterocyclic ring optionally containing, in addition to said nitro groups, a hydroxy, methyl or methoxy group.

2. A polymer according to claim 1 wherein the recurring unit of the polymer has the formula

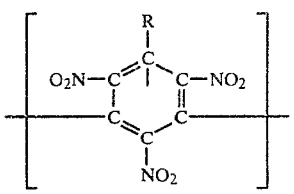

wherein R is hydrogen or methyl.

3. A polymer having the recurring unit which is the divalent radical of a compound of the formula

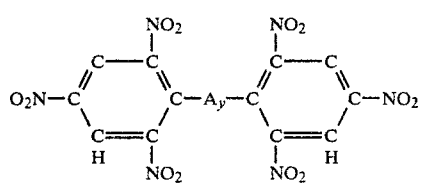

wherein

A represents oxygen or a moiety of the group

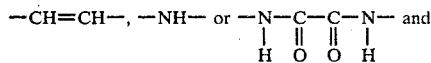

y=0 or 1,
said divalent radical being formed by removal of 2 hydrogen atoms bonded to carbocyclic carbon atoms, having at least four recurring units.

4. A polymer according to claim 1 wherein the recurring unit consists of a dinuclear or polynuclear nitrated ring, one of the rings containing one or more hetero atoms.

5. A polymer according to claim 1 having between 4 and 12 recurring units.

6. A homopolymer having a recurring unit of the formula

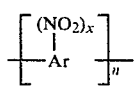

wherein
x is 2 to 3,
n is 4 to 20 and
Ar is a methyl, methoxy, or hydroxy substituted or unsubstituted arylene radical, fused arylene-heterocyclic radical or a divalent heterocyclic radical where the hetero atom is oxygen, nitrogen, or sulfur.

7. A homopolymer according to claim 6 having a molecular weight of between 800 and 4500 said molecular weight determined by gel chromatography.

8. A homopolymer according to claim 6 wherein Ar is a divalent arylene radical having between 6 and 4 carbocyclic carbon atoms.

9. A homopolymer according to claim 8 wherein Ar is a single ring or fused diaryl radical.

10. A homopolymer according to claim 8 wherein Ar is a heterocyclic radical having 3 to 13 carbocyclic carbon atoms and having as the hetero atom oxygen, nitrogen or sulphur.

11. A homopolymer according to claim 10 wherein Ar is a fused heterocyclic radical.

12. A process for preparing a polymer of claim 1 which comprises contacting a mononuclear, dinuclear or polynuclear aromatic or heterocyclic compound containing at least 2 nitro groups and at least 2 halogen atoms on the ring at an elevated temperature with copper.

13. A process according to claim 12 wherein said aromatic or heterocyclic compound is contacted with a said copper in the presence of a solvent.

14. A process according to claim 12 wherein the aromatic or heterocyclic compound is contacted with the copper at a temperature between 150° and 250° C.

15. A process according to claim 12 wherein the reaction is performed employing a compound of the formula

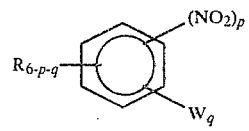

in which R represents hydrogen or methyl and W represents a halogen, and p and q can individually be equal to 2 or 3.

16. A process for preparing a polymer which comprises contacting a compound of the formula

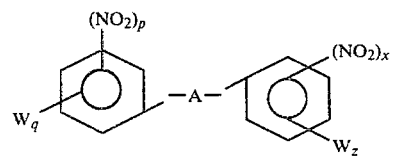

in which
A is —O—, —CH=CH—, —NH—, or

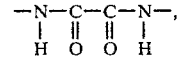

W represents a halogen,
p, q, x, and z each individually represent values of 2 or 3
with copper at an elevated temperature.

17. A polymer according to claim 3 wherein A represents —CH=CH—.

18. A polymer according to claim 3 wherein A represents —NH—.

19. A polymer according to claim 3 wherein A represents

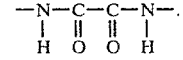

20. A polymer according to claim 3 wherein A is —O—.